US011026650B2

(12) United States Patent
Duewer

(10) Patent No.: US 11,026,650 B2
(45) Date of Patent: Jun. 8, 2021

(54) METHODS, SYSTEMS, APPARATUSES, AND COMPUTER PROGRAM PRODUCTS FOR AUTOMATICALLY DETERMINING EXPOSURE TIME FOR AN INTRAORAL IMAGE

(71) Applicant: DENTSPLY SIRONA Inc., York, PA (US)

(72) Inventor: Frederick W. Duewer, Woodside, NY (US)

(73) Assignee: DENTSPLY SIRONA Inc., York, PA (US)

( * ) Notice: Subject to any disclaimer, the term of this patent is extended or adjusted under 35 U.S.C. 154(b) by 191 days.

(21) Appl. No.: 16/239,570

(22) Filed: Jan. 4, 2019

(65) Prior Publication Data

US 2019/0209117 A1 Jul. 11, 2019

Related U.S. Application Data

(60) Provisional application No. 62/615,644, filed on Jan. 10, 2018.

(51) Int. Cl.
*A61B 6/00* (2006.01)
*A61B 6/14* (2006.01)
*A61B 6/02* (2006.01)

(52) U.S. Cl.
CPC .............. *A61B 6/542* (2013.01); *A61B 6/025* (2013.01); *A61B 6/145* (2013.01); *A61B 6/467* (2013.01);

(Continued)

(58) Field of Classification Search
CPC ......... A61B 6/542; A61B 6/025; A61B 6/145; A61B 6/467; A61B 6/488; A61B 6/5211; A61B 6/5235; A61B 6/5258; A61B 6/545
See application file for complete search history.

(56) References Cited

U.S. PATENT DOCUMENTS

| | | | |
|---|---|---|---|
| 2004/0101087 A1* | 5/2004 | Hsieh | A61B 6/032 378/4 |
| 2009/0168966 A1* | 7/2009 | Suzuki | A61B 6/4233 378/116 |

(Continued)

FOREIGN PATENT DOCUMENTS

| | | |
|---|---|---|
| EP | 2878268 A1 | 6/2015 |
| WO | 2016044465 A1 | 3/2016 |

OTHER PUBLICATIONS

International Search Report; PCT/US2019/012243; Apr. 30, 2019 (completed); dated May 9, 2019.

(Continued)

*Primary Examiner* — Christine S. Kim
(74) *Attorney, Agent, or Firm* — Dentsply Sirona Inc.

(57) ABSTRACT

A method, apparatus, system, and computer program product for automatically determining exposure time for an intraoral image. The method includes acquiring a low dose pilot projection image of an object to be imaged, performing a sanity check to ensure that a usable exposure is attainable, estimating a remaining exposure time required for an additional projection image, taking the additional projection image and adding the two images together to generate a final image wherein the dose delivered to the x-ray detector is influenced by patient specific dental anatomy.

20 Claims, 10 Drawing Sheets

(52) U.S. Cl.
    CPC ............ *A61B 6/488* (2013.01); *A61B 6/5211* (2013.01); *A61B 6/5235* (2013.01); *A61B 6/5258* (2013.01); *A61B 6/545* (2013.01)

(56) References Cited

U.S. PATENT DOCUMENTS

| | | | |
|---|---|---|---|
| 2010/0310037 A1* | 12/2010 | Wang | A61B 6/06 378/6 |
| 2012/0307965 A1* | 12/2012 | Bothorel | A61B 6/4452 378/10 |
| 2012/0314834 A1* | 12/2012 | Yao | G01N 23/087 378/5 |
| 2015/0190102 A1* | 7/2015 | Bruno | A61B 6/542 378/39 |
| 2018/0014803 A1* | 1/2018 | Schneider | A61B 5/055 |
| 2018/0103920 A1* | 4/2018 | Ito | A61B 6/54 |

OTHER PUBLICATIONS

Written Opinion of the International Searching Authority; PCT/US2019/012243; Apr. 30, 2019 (completed); dated May 9, 2019.
International Preliminary Report on Patentability; PCT/US2019/012243; Apr. 30, 2019 (completed); dated May 9, 2019.

\* cited by examiner

METHODS, SYSTEMS, APPARATUSES, AND COMPUTER PROGRAM PRODUCTS FOR AUTOMATICALLY DETERMINING EXPOSURE TIME FOR AN INTRAORAL IMAGE

CROSS REFERENCE TO RELATED APPLICATIONS

This application claims benefit of provisional application 62/615,644, filed on Jan. 10, 2018 which is incorporated herein by reference in its entirety.

FIELD

The present application relates generally to obtaining x-ray images in a dental environment, and, more particularly, to a method, system, apparatus, and computer program product for utilizing an automatic exposure control in the creation of intraoral images in an intraoral imaging system wherein the dose delivered to an x-ray sensor/detector is consistent and primarily influenced by dental anatomy.

BACKGROUND

X-ray radiography can be performed by positioning an x-ray source on one side of an object (e.g., a patient or a portion thereof) and causing the x-ray source to emit x-rays through the object and toward an x-ray detector located on the other side of the object. As the x-rays pass through the object from the x-ray source, their energies are absorbed to varying degrees depending on the composition of the object, and x-rays arriving at the x-ray detector form a two-dimensional (2D) x-ray image or projection image (also known as a radiograph) based on the cumulative absorption through the object.

Intraoral radiography is a technique in which an imaging sensor/detector is placed inside the mouth of a patient and an x-ray source outside the mouth is used to irradiate the sensor/detector with x-rays. The x-ray attenuation of hard tissues in the mouth results in a clinical image being formed on the detector. Several considerations apply to the exposure time used in the collection of clinical images.

First, increasing the applied x-ray dose typically improves the number of x-ray photons contributing to the image. Given that x-ray images are typically dominated by Poisson noise, the signal-to-noise ratio (SNR) improves as additional x-ray dose is applied. A minimum x-ray dose is therefore typically required to successfully visualize a given feature of clinical interest. Beyond that dosage, increasing dosage does not necessarily result in significant additional clinical utility.

Second, x-ray absorption in tissue results in the ionization of atoms in tissue and thereby the breaking down and reforming of chemical bonds. X-ray exposure has typically been shown to increase cancer risk and thereby mortality. There is therefore a need to eliminate excessive x-ray exposure. Moreover, typical x-ray sensors are subject to saturation wherein, if the amount of energy absorbed by the x-ray sensor exceeds a sensor-dependent threshold, the detector pixels returns their maximum value. The saturated region of the image therefore contains little clinically relevant information.

These problems have been solved in the past by setting intraoral x-ray exposures manually. Fixed settings based on nominal source characteristics, expected x-ray filtration, expected source-detector separation, expected patient characteristics, expected x-ray sensor characteristics have been included in x-ray systems for manual selection. There are several issues with this approach. First, typical x-ray sources vary appreciably in output, both upon construction and over their useful lifetime. Second, the source position is typically determined manually and inexactly, leading to appreciable variation in the delivered dose. Third, patient characteristics vary appreciably, leading to variations in the dose delivered to the sensor. These variations result in variations in image quality which can impact diagnostic performance.

Therefore, it would be desirable to have a system, method, apparatus, and computer program product which allow for the automatic control of exposure settings in an intraoral imaging system.

SUMMARY

Existing limitations associated with the foregoing, as well as other limitations, can be overcome by methods for automatically determining the necessary exposure time for a given intraoral image, and by systems, apparatuses, and computer programs that operate in accordance with the methods.

According to an example embodiment herein, a method for automatically determining the necessary exposure time for a given intraoral image comprises acquiring a low dose pilot projection image of an object to be imaged, performing a sanity check to ensure that a usable exposure is attainable, estimating remaining exposure time for an additional projection image, checking to ensure that the additional projection image will not be saturated, taking the additional projection image using the estimated remaining exposure time and adding the two images together to form a final image.

In one example embodiment herein, the acquisition includes performing a setup comprising inputting an expectation of the quality of the image to be acquired wherein the expectation could be discrete, for example Low, Standard or High Quality and wherein a default expectation could be Standard Quality. The expectation may alternatively be according to a sliding scale. A dark field image may then be taken after which a low dose pilot projection image is acquired. The dark field image is then subtracted from the low dose pilot projection image to remove effects of dark current in the pilot projection image.

In another example embodiment herein, the sanity check comprises calculating a cumulative histogram of all gray level values of pixels of said pilot projection image and testing for unacceptable exposure conditions. In a further example embodiment herein, estimating the remaining required exposure time includes determining the pilot projection image range of all gray level values of pixels of said pilot projection image and calculating a high threshold and a low threshold using the determined range. Also in a further example embodiment herein, calibration results may be used to estimate a typical value for an air gap and used to inform the high threshold determination. In another example embodiment herein, the estimation of the remaining exposure time includes determining a median value of all gray level values of pixels between the determined high and low thresholds.

In an example embodiment herein, the estimation of the remaining exposure time includes determining an optimal exposure time using a target value, the determined median and the pilot projection image exposure time.

In another example embodiment herein, the method further comprises ensuring that the resulting image is not saturated. This may involve determining an estimated saturation exposure time, determining an estimated exposure time and checking whether the estimated exposure time is less than a minimum settable exposure time.

In yet another example embodiment herein, the method further comprises taking an additional projection image and adding the pilot projection image and the additional projection image together wherein the additional projection image is taken using the estimated remaining exposure time, the dark field image is subtracted from the additional projection image and the resulting image and the low dose pilot projection image are summed to form a final image for an x-ray system. In a tomosynthesis x-ray system, multiple projections are taken (e.g. 41 projections at varying angles), as such multiple additional projection images can be taken after the pilot projection image is taken. Since the angles at which the multiple projection images are taken in a tomosynthesis x-ray system changes, the pilot projection image may not be combined with the additional projection images. Instead an appropriate remaining exposure time for each additional projection image may be determined from the single pilot projection such that each additional projection image is itself a final image. Therefore the combination of a pilot projection image and an additional projection image will not be needed for a tomosynthesis x-ray system of the disclosure. In a further embodiment, gain and bad pixel correction may be applied to the final image. A spot remover may also be applied. In yet another embodiment at least the final image(s) may be reconstructed into tomographic images. In a further embodiment the reconstructed tomographic images may be tomosynthesis images. In another embodiment herein, the tomographic images may be displayed on a display unit. In a further embodiment herein, the quality of exposure can be displayed on a display unit.

These methods may be useful for delivering a dose to a sensor wherein said dose is consistent and mostly influenced by dental anatomy since otherwise, variations in x-ray source position, clinical features of the patient, and x-ray source output can cause the dose delivered to a sensor to vary appreciably.

Further features and advantages, as well as the structure and operation of various embodiments herein, are described in detail below with reference to the accompanying drawings.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

Figure 1:
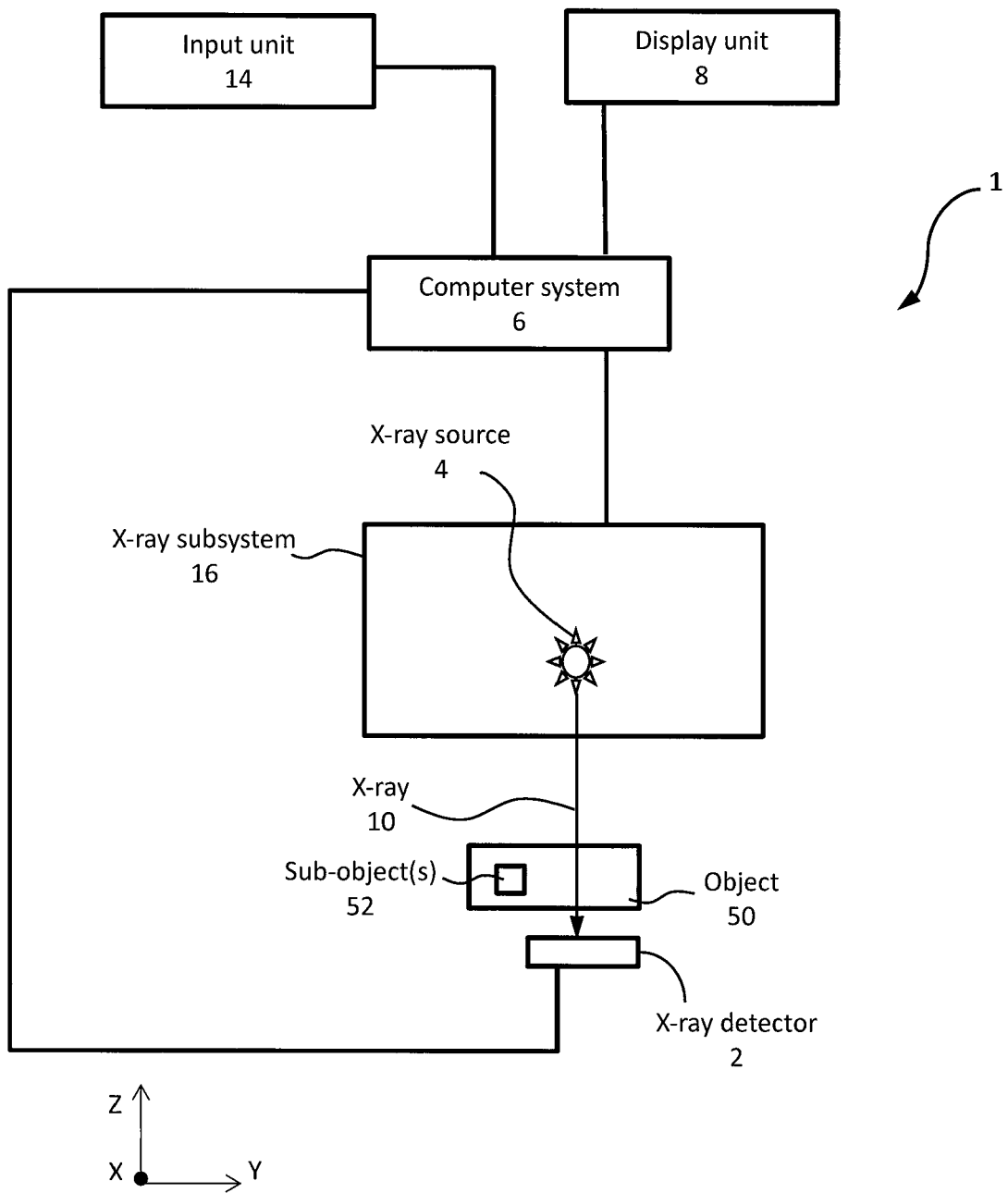
FIG. 1 is a system block diagram of an intraoral x-ray system according to one example embodiment herein.

Different ones of the Figures may have at least some reference numerals that are the same in order to identify the same components, although a detailed description of each such component may not be provided below with respect to each Figure.

DETAILED DESCRIPTION

In accordance with example aspects described herein, methods, systems, apparatuses, and computer programs are provided for automatically determining the necessary exposure time for a given intraoral image.

Intraoral X-Ray System and Intraoral Tomosynthesis X-Ray System

FIG. 1 illustrates a block diagram of an intraoral x-ray system 1 for obtaining an intraoral images, and which is constructed and operated in accordance with at least one example embodiment herein. The system 1 can be operated to obtain one or more x-ray images of an object 50 of interest, which may further include one or more sub-object(s) 52. For example, object 50 may be a tooth (or teeth) and surrounding dentition of a patient, and sub-object(s) 52 may be root structures within the tooth.

The system 1 includes an x-ray detector 2 and an x-ray subsystem 16, both of which, including subcomponents thereof, are electrically coupled to a computer system 6. In one example, the x-ray subsystem 16 hangs from a ceiling- or wall-mounted mechanical arm (not shown), so as to be freely positioned relative to an object 50. The x-ray subsystem 16 further includes an x-ray source 4.

The computer system 6 may be electrically coupled to a display unit 8 and an input unit 14. The display unit 8 may be an output and/or input user interface.

The x-ray detector 2 is positioned on one side of the object 50 and the receiving surface of the x-ray detector 2 extends in an x-y plane in a Cartesian coordinate system. The x-ray detector 2 can be a small intraoral x-ray sensor that includes, for example, a complementary metal-oxide semiconductor (CMOS) digital detector array of pixels, a charge-coupled device (CCD) digital detector array of pixels, or the like. In an example embodiment herein, the size of the x-ray detector 2 varies according to the type of patient to whom object 50 belongs, and more particularly, the x-ray detector 2 may be one of a standard size employed in the dental industry. Examples of the standard dental sizes include a "Size-2" detector, which is approximately 27×37 mm in size and is typically used on adult patients, a "Size-1" detector, which is approximately 21×31 mm in size and is typically used on patients that are smaller than Size-2 adult patients, and a "Size-0" detector, which is approximately 20×26 mm in size and is typically used on pediatric patients. In a further example embodiment herein, each pixel of the x-ray detector 102 has a pixel width of 15 μm, and correspondingly, the Size-2 detector has approximately 4 million pixels in a 1700×2400 pixel array, the Size-1 detector has approximately 2.7 million pixels in a 1300×2000 pixel array, and the Size-0 detector has approximately 1.9 million pixels in a 1200×1600 pixel array. The color resolution of the x-ray detector 2 may be, in one example embodiment herein, a 12-bit grayscale resolution, although this example is not limiting, and other example color resolutions may include an 8-bit grayscale resolution, a 14-bit grayscale resolution, and a 16-bit grayscale resolution.

The x-ray source 4 is positioned on an opposite side of the object 50 from the x-ray detector 2. The x-ray source 4 emits x-rays 10 which pass through object 50 and are detected by the x-ray detector 2. The x-ray source 4 is oriented so as to emit x-rays 10 towards the receiving surface of the x-ray detector 2 in at least a z-axis direction of the Cartesian coordinate system, where the z-axis is orthogonal to the x-y plane associated with the receiving surface of the x-ray detector 2. A scout shot is taken to obtain a pilot projection image. Subsequently, one additional projection image is taken using an estimated remaining exposure time obtained from the autoexposure steps discussed herein. The pilot projection image and the additional image can then be combined to form a final image.

In one embodiment as shown in FIG. 1, only a single exposure may be taken and the resulting image on the detector read.

Figure 2:
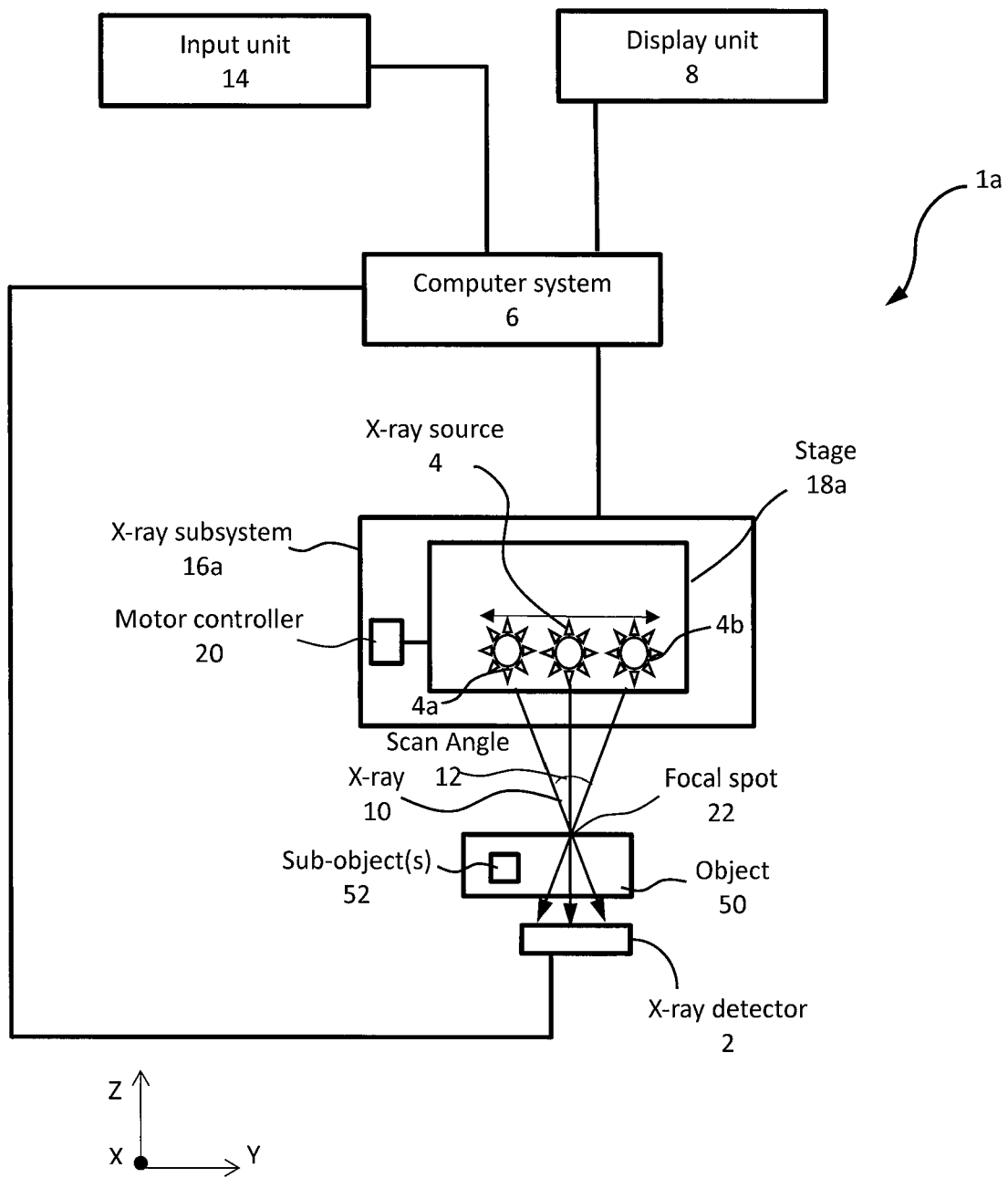
FIG. 2 is a system block diagram of an intraoral tomosynthesis x-ray system according to one example embodiment herein.

In a further embodiment according to FIG. 2, which shows a tomosynthesis x-ray system 1a, the x-ray source 4 may also emit x-rays 10 while positioned at each of multiple different locations within a scan angle 12, where a $_0°$ position in the scan angle 12 corresponds to the position for emitting x-rays 10 along the x-z plane. The tomosynthesis x-ray subsystem 16a may include an x-ray source 4 which may be mounted on a stage 18a. In one example embodiment herein, the x-ray subsystem 16a, and hence, also the x-ray source 4, is initially positioned to the 0° position. A scout shot is taken to obtain a pilot projection image at the 0° position. The x-ray source is then positioned to a predetermined starting position relative to the object 50. The computer system 6 then controls the on-board motor controller 20 to move the x-ray source 104 via the motorized stage 18a, based on the known starting position, to step through each of the different locations within the scan angle 12 to take additional images using an estimated exposure time obtained from the autoexposure steps discussed herein. The computer system 6 may first control the x-ray source 4 to cause the x-ray source 4 to emit x-rays 10 to take a single pilot shot in order to determine appropriate exposure time(s) to use for taking additional shots at each of those different locations within the scan angle 12. Since the angles at which the multiple additional projection images are taken in the tomosynthesis x-ray system changes, the pilot projection image may not be combined with the additional projection images. Instead an appropriate remaining exposure time for each additional projection image may be determined from the single pilot shot such that each additional projection image is itself a final image. The x-rays 10 emitted from each of the different locations within the scan angle 12 may converge substantially at a tomographic focal spot 22. The tomographic focal spot 22 may be, for example, located close to the detector such that x-rays 10 emitted from the x-ray source 4 positioned at the outer limits of the scan angle 12 are aimed at and do not miss the x-ray detector 2.

As emitted x-rays 110 pass through the object 50, photons of x-rays 10 will be more highly attenuated by high density structures of the object 50, such as calcium-rich teeth and bone, and less attenuated by soft tissues, such as gum and cheek. One or more of the attenuating structures can be represented by sub-object(s) 52. X-rays 10 passing through and attenuated by object 50, are projected onto x-ray detector 2, which converts the x-rays 10 into electrical signals and provides the electrical signals to computer system 6. In one example embodiment, the x-ray detector 2 may be an indirect type of detector (e.g., a scintillator x-ray detector) that first converts x-rays 10 into an optical image and then converts the optical image into the electrical signals, and in another example embodiment, the x-ray detector 2 may be a direct type of detector (e.g., a semiconductor x-ray detector) that converts x-rays 10 directly into the electrical signals. The computer system 6 processes the electrical signals to form a two-dimensional projection image of the object 50 in a known manner. In one example embodiment herein, the image size of the two-dimensional projection image corresponds to the dimensions and the number of pixels of the x-ray detector 2.

The computer system 6 processes the plurality of final images to reconstruct a series of tomographic images which are two-dimensional tomosynthesis image slices, also known as a tomosynthesis stack of images. By utilizing said autoexposure means, a single pilot projection image may be taken to determine the correct dose for all images to be taken in the tomosynthesis scan in said tomosynthesis system 1a in order to limit unnecessary exposure to x-rays.

Computer System for X-Ray and Tomosynthesis X-Ray Imaging Using Autoexposure

Having described systems 1 and 1a for acquiring an x-ray dataset and a tomosynthesis dataset respectively, reference will now be made to FIG. 3, which shows a block diagram of a computer system 100 that may be employed in accordance with at least some of the example embodiments herein. Although various embodiments are described herein in terms of this exemplary computer system 100, after reading this description, it will become apparent to a person skilled in the relevant art(s) how to implement the disclosure using other computer systems and/or architectures.

Figure 3:
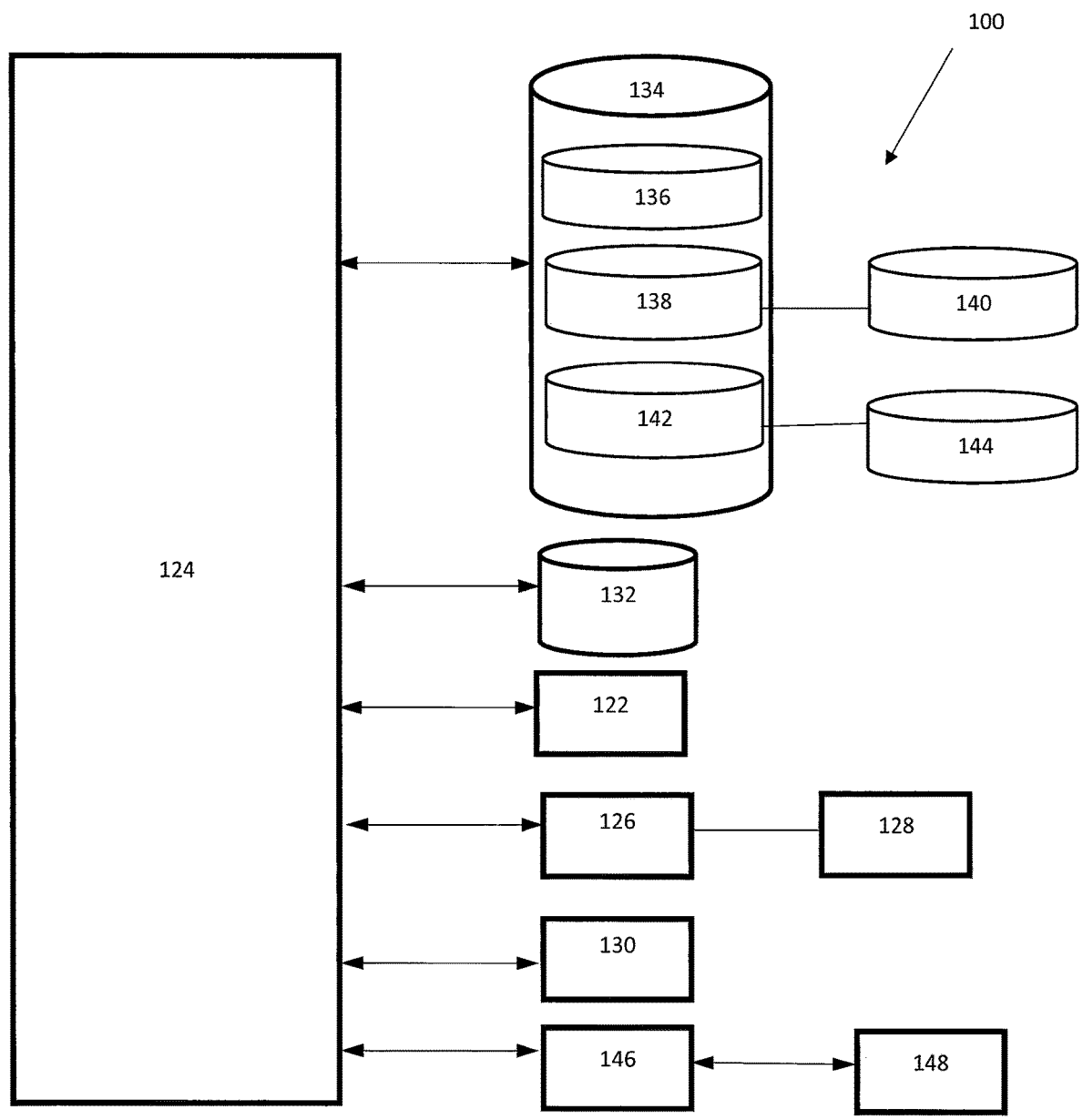
FIG. 3 illustrates a block diagram of an example computer system of the systems shown in FIG. 1 and FIG. 2.

FIG. 3 illustrates a block diagram of the computer system 100. In one example embodiment herein, at least some components of the computer system 100 (such as all those components, or all besides component 128) can form or be included in the system 1, 1a shown in FIG. 1 and FIG. 2. The computer system 100 includes at least one computer processor 122 (also referred to as a "controller"). The computer processor 122 may include, for example, a central processing unit, a multiple processing unit, an application-specific integrated circuit ("ASIC"), a field programmable gate array ("FPGA"), or the like. An FPGA, for example, may be used to communicate with X-ray detector 2. The processor 122 is connected to a communication infrastructure 124 (e.g., a communications bus, a cross-over bar device, or a network).

The computer system 100 may also include a display interface (or other output interface) 126 that forwards video graphics, text, and other data from the communication infrastructure 124 (or from a frame buffer (not shown)) for display on a display unit 128 (which, in one example embodiment, can form or be included in the display unit 108). For example, the display interface 126 may include a video card with a graphics processing unit.

The computer system 100 also includes an input unit 130 that can be used by a user of the computer system 100 to send information to the computer processor 122. In one example embodiment herein, the input unit 130 can form or be included in the input unit 14 of FIGS. 1 and 2. For example, the input unit 130 can include a keyboard device and/or a mouse device or other input device. In one example, the display unit 128, the input unit 130, and the computer processor 122 can collectively form a user interface.

In an example embodiment that includes a touch screen, for example, the input unit 130 and the display unit 128 can be combined, or represent a same user interface. In such an embodiment, a user touching the display unit 128 can cause corresponding signals to be sent from the display unit 128 to the display interface 126, which can forward those signals to a processor such as processor 122, for example. In an example embodiment herein, a system with a wall-mounted mechanical arm (not shown) may have a module attached to a wall wherein the module includes a processor 122 and on board electronics for controlling the x-ray source 4, a motorized stage 18*a* and communicating with the detector 2. Processor 122 can be configured to perform part (or all) of any of the procedures described herein. For example, one or more steps of the procedure illustrated in FIGS. 4-9 can be stored on a non-transitory storage device in the form of computer-readable program instructions. To execute a procedure, the processor 122 loads the appropriate instructions, as stored on storage device, into memory 132, and then executes the loaded instructions.

In addition, the computer system 100 includes a main memory 132, which preferably is a random access memory ("RAM"), and also may include a secondary memory 134. The secondary memory 234 can include, for example, a hard disk drive 136 and/or a removable-storage drive 138 (e.g., a floppy disk drive, a magnetic tape drive, an optical disk drive, a flash memory drive, and the like). The removable-storage drive 138 reads from and/or writes to a removable storage unit 140 in a well-known manner. The removable storage unit 140 may be, for example, a floppy disk, a magnetic tape, an optical disk, a flash memory device, and the like, which is written to and read from by the removable-storage drive 138. The removable storage unit 140 can include a non-transitory computer-readable storage medium storing computer-executable software instructions and/or data.

In alternative embodiments, the secondary memory 134 can include other computer-readable media storing computer-executable programs or other instructions to be loaded into the computer system 100. Such devices can include a removable storage unit 144 and an interface 142 (e.g., a program cartridge and a cartridge interface similar to those used with video game systems); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also can include a communications interface 146 that enables software and data to be transferred between the computer system 100 and external devices. Examples of the communications interface 146 include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCMCIA") interface, and the like. Software and data transferred via the communications interface 146 can be in the form of signals, which can be electronic, electromagnetic, optical or another type of signal that is capable of being transmitted and/or received by the communications interface 146. Signals are provided to the communications interface 146 via a communications path 148 (e.g., a channel). The communications path 148 carries signals and can be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs (also referred to as computer control logic) are stored in the main memory 132 and/or the secondary memory 134. The computer programs also can be received via the communications interface 146. The computer programs include computer-executable instructions which, when executed by the computer processor 122, cause the computer system 100 to perform the all or part of the processes as described herein and shown in FIGS. 4-9, for example. Accordingly, the computer programs can control the computer system 106 and other components (e.g., the x-ray detector 2 and the x-ray source 4) of the intraoral x-ray system 1 or intraoral tomosynthesis x-ray system 1*a*.

In one example embodiment herein, the software can be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the intraoral x-ray 1 or tomosynthesis system 1*a*, to perform the processes described herein.

In another example embodiment hardware components such as ASICs, FPGAs, and the like, can be used to carry out the functionality described herein. Implementation of such a hardware arrangement so as to perform the functions described herein will be apparent to persons skilled in the relevant art(s) in view of this description.

Method for Determining the Necessary Exposure Time for an Intraoral Image

Figure 4:
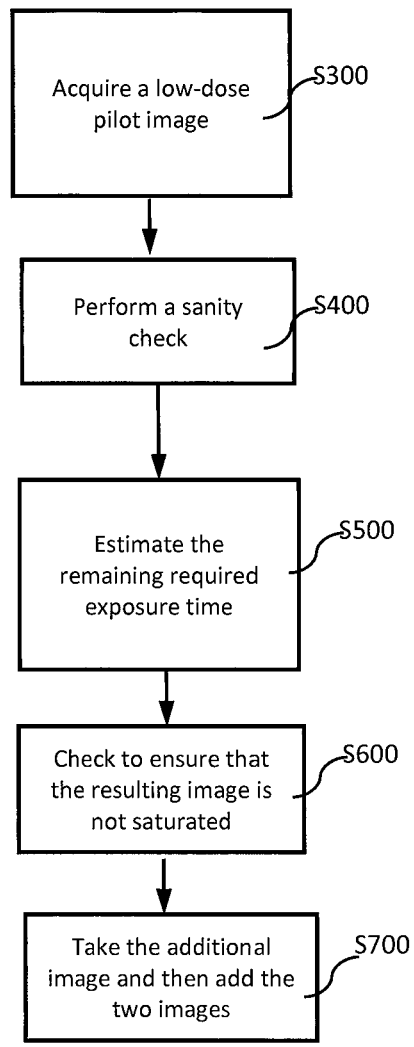
FIG. 4 is a diagram illustrating autoexposure steps according to an example embodiment herein.
Figure 5:
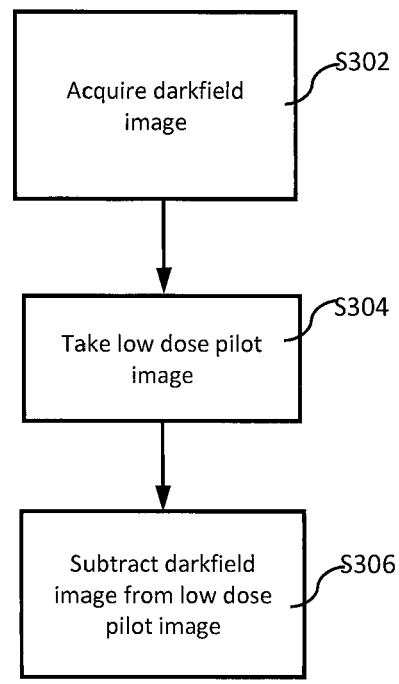
FIG. 5 is a diagram illustrating the how a pilot projection image is taken.
Figure 6:
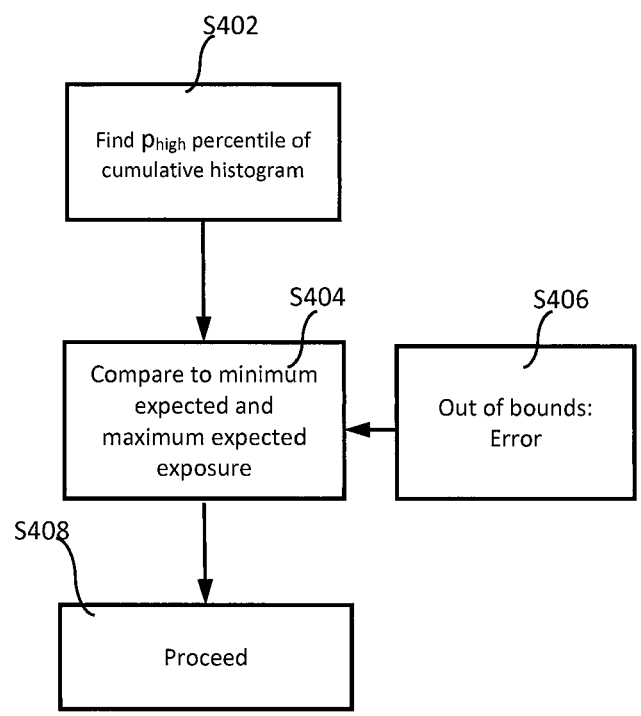
FIG. 6 is a diagram illustrating how to perform a sanity check to ensure that a usable exposure is attainable.

Having described the computer system 100 of FIG. 3, the intraoral x-ray system 1 and intraoral tomosynthesis x-ray system 1*a*, will now be further described in conjunction with FIG. 4, which shows a flow diagram of a process according to an example embodiment herein for using a pilot projection to guide a process for determining exposure time for an intraoral image and deliver a dose to a sensor wherein said dose is consistent and mostly influenced by dental anatomy.

In Step S300 the system 1, 1*a* acquires a low dose pilot projection image of object 50. The computer system 6 then performs a sanity check to test for unacceptable exposure conditions in Step S400. In Step S500, an estimation of a remaining exposure time is determined. A resulting image is then analyzed for saturation in Step S600. Finally an additional projection image is then taken and used to create a final image by summing the additional projection image and the low dose pilot projection image in Step S700. These steps will be discussed in more detail hereinafter.

In Step S300, the system 1, 1*a* acquires a low dose pilot projection image. In one example embodiment herein, a dark field image is read S302. This is accomplished by reading out the output of detector 2 with the x-ray source 4 turned off. Subsequently, a low dose pilot projection image of object 50 is taken using the x-ray source 4. In a tomosynthesis system 1*a*, the low dose pilot projection image can be taken in the position of a center projection, that is, 0° to the z-axis direction, where the z-axis is orthogonal to the x-y plane associated with the receiving surface of the x-ray detector as shown in FIG. 2. The dark field image is then subtracted from the low dose pilot projection image in Step S306 to remove image contributions associated with dark current. In an example embodiment herein the noise on the detector 2 is dominated by Poisson noise. In another embodiment herein, a number of defective pixels is significantly less than 1% of the total pixels.

In Step S400, a sanity check is performed to ensure that a usable exposure is attainable. In one example embodiment herein, the computer system 6 computes a histogram gray level values of pixels of the pilot projection image and removes fixed portions of the histogram corresponding to metal and tissue regions of the dental anatomy. By removing fixed portions of the histogram range corresponding to metal and tissue regions, and calculating the median of the histogram, the calculated median can be used to estimate the exposure time for a second image. Dental anatomy often has uniform, very low transmission metallic regions. Dental anatomy also has uniform, very high transmission, tissue regions. Both of these regions type can occupy significant fractions of the image and thereby bias algorithms. However, assuming that any metal or tissue will be relatively close to one ends of the histogram, one can remove from consideration a fraction of the total histogram range corresponding to the metal and tissue regions as well as the fraction of the total histogram range corresponding to defective pixels. The remaining pixels values will not contain metal or tissue contributions and are thereby representative of clinical regions. The median of the remaining pixel gray level values represents the teeth and trabeculae. In another embodiment, an average of the remaining pixel gray level values may represent the teeth and trabeculae. The computer system 6 may perform the sanity check according to the following steps:

1. An estimated scale factor (K) is calculated using the exposure time for the pilot projection image ($T_{pilot}$) and a nominal/typical exposure time ($T_{nominal}$).

$$K=T_{pilot}/T_{nominal}.$$

The typical/nominal exposure time can be arbitrary for example, 150 msec.

Figure 10:
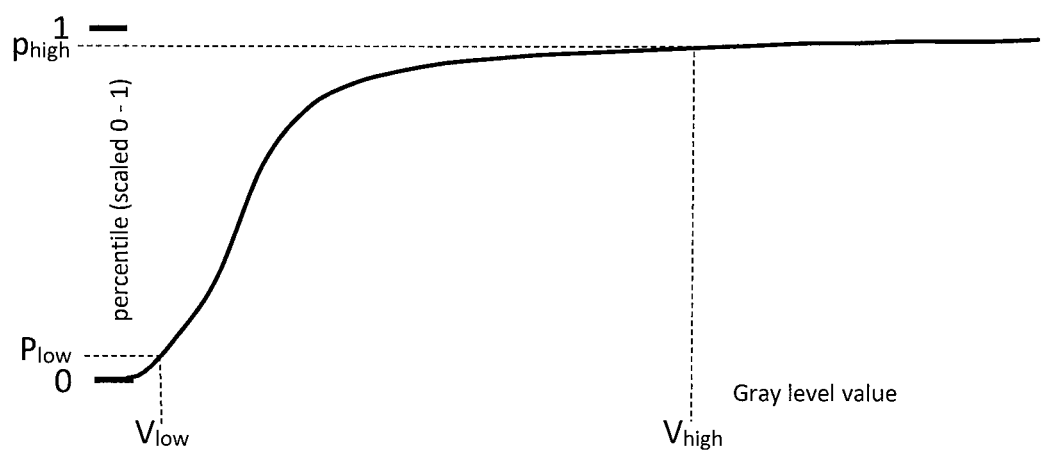
FIG. 10 is a diagram illustrating how a cumulative histogram according to an embodiment described herein.

2. A cumulative histogram of the pilot projection image is then computed as shown in FIG. 10.

3. A $p_{high}$ percentile (with corresponding gray level value, $V_{high}$) and a $p_{low}$ percentile (with corresponding gray level value $V_{low}$) of the cumulative histogram is determined wherein $p_{high}$ is a percentile used to determine an upper limit of the gray level values of the image and $p_{low}$ is a percentile used to determine a lower limit of gray level values of the image. This is to remove contributions of defective pixels to the gray level values of the image.

In an example embodiment herein, gray level values outside $p_{low}$ to $p_{high}$ percentiles correspond defective pixels and gray level values inside $p_{low}$ to $p_{high}$ percentiles correspond to teeth, trabeculae and metal and tissue regions of the dental anatomy. In an example embodiment $p_{high}$ may be between 70 to 99.5$^{th}$ percentile. In a further embodiment $p_{low}$ may be between 0.5 and 30$^{th}$ percentile.

4. Unacceptable exposure conditions are tested for by comparing (as shown in Step S404) $V_{high}$ with the maximum metal value and the maximum exposure value. The maximum metal value is the largest pixel count or gray level value expected to correspond to metal, typically 500. The maximum exposure value is the largest pixel count or gray level value expected for a sensor imaged at nominal exposure time and position, typically 4095.

For the preambles above, it can be deduced that:

a. If $V_{high}<M_{metal}*K$, the exposure will not be usable. In an embodiment herein, the sanity check will return an error indicating unacceptably low x-ray exposure as in Step S406.

b. If $V_{high}>M_{exposure}*K$, the exposure will also not be usable and an error indicating unacceptably high x-ray exposure can be returned as in Step S406.

Figure 7:
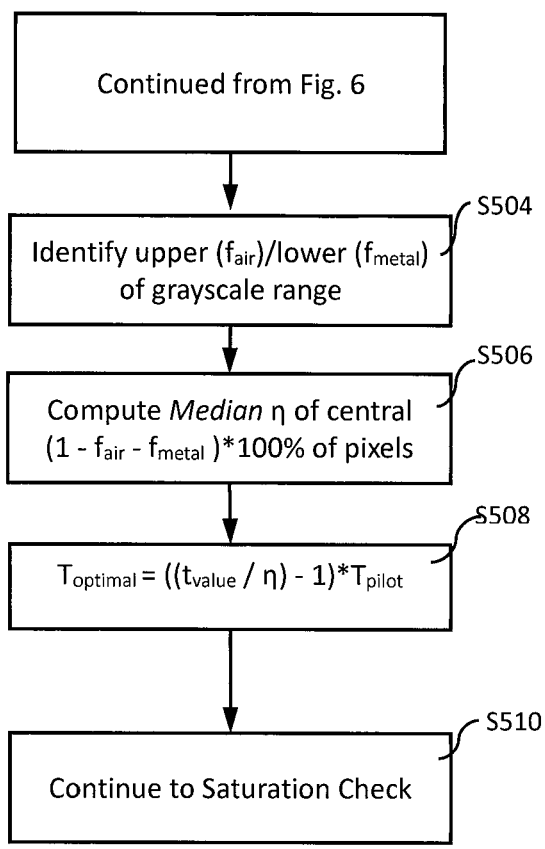
FIG. 7 is a diagram that illustrates how to estimate a remaining exposure time.

Turning now to FIG. 7, the computer system 6 can estimate the optimal remaining exposure time required by identifying and removing contributions by metal and tissue regions of the dental anatomy to the gray level values of the cumulative histogram as in step S504 after contributions by defective pixels have been removed. A median of the remaining gray level values is then computed in step S506 wherein the median represents the teeth and trabeculae. Using a target gray level value, the remaining exposure time can be calculated in step S508 for a saturation check in step S510. In an example embodiment herein, the estimation of the remaining exposure time $T_{est}$ can be determined by first determining an estimated optimal remaining exposure time $T_{optimal}$ according to the following steps.

1. Determine the pilot projection image range ($\Delta$) where the image range $\Delta=V_{high}-V_{low}$ and wherein $V_{high}$ is gray level value corresponding to the $p_{high}$ percentile of the pilot projection image and $V_{low}$ is the gray level value corresponding to the $p_{low}$ percentile of the pilot projection image as shown in FIG. 10.

2. Determine a high threshold ($\tau_{high}$) and a low threshold ($\tau_{low}$) using the computed range $\Delta$.

$$\tau_{high}=V_{high}-f_{air}*\Delta$$

$$\tau_{low}=V_{low}+f_{metal}*\Delta$$

wherein $\tau_{high}$ represents the upper limit of the filtered cumulative histogram wherein contributions by metal and tissue regions of the dental anatomy and defective pixels of the detector 2 have been removed and wherein $\tau_{low}$ represents the lower limit of the filtered cumulative histogram wherein contributions by metal and tissue regions of the dental anatomy and defective pixels of the detector 2 have been removed. Herein, $f_{air}$ is a fraction of the image range $\Delta$ assumed to be attributable to air and tissues of the dental anatomy while $f_{metal}$ is a fraction of the image range assumed to be attributable to metal regions of the dental anatomy. In an example embodiment herein $f_{air}$ is between 5-35% and in a further example embodiment $f_{metal}$ is also between 5-35%.

3. Subsequently, the median ($\eta$) value of all of the pixels between the high and low thresholds can be computed.

4. The estimated optimal remaining exposure time ($T_{optimal}$) can be determined using a target final image gray level median value, $t_{value}$, the median value and the pilot projection image exposure time.

In an embodiment herein, $t_{value}$ is 1200. $t_{value}$ is chosen such that the corresponding remaining exposure to be taken may be summed with the pilot projection image to produce a final image having a cumulative histogram that has a median value close or equal to the target value $t_{value}$. With this, the estimated optimal remaining exposure time $T_{optimal}$ may be determined as follows.

$$T_{optimal}=((t_{value}/\eta)-1)*T_{pilot}$$

where $\eta$ is the median value of all of the pixels between the high and low thresholds and $T_{pilot}$ is the exposure time of the pilot projection image. It can be seen that if is larger than $t_{value}$, $T_{optimal}$ will be negative. This can be prevented by increasing the detector to x-ray source distance if necessary to produce a corresponding decrease in the median gray level value η. In a tomosynthesis x-ray system, $t_{value}$ may be chosen such that each additional projection image is a final image that does not need to be summed with the pilot projection image.

It will be appreciated by a person of ordinary skill in the art that values such as $t_{value}$, saturation value of 4095, metal value of 500 and maximum exposure value of 4095 are detector dependent and as such will vary according to the detector type used. Specifically, design decisions of the detector used such as bit depth, dynamic range and typical fraction of the detector dynamic range may affect the values. For example, the saturation value may be chosen to match the bit depth/the highest grey level value obtainable for the detector being used. $t_{value}$ may be chosen to match the expected gray level values required to obtain clinically meaningful images under nominal/typical operating conditions. The metal value may be chosen to match exposure values of metallic objects and the maximum exposure value may be chosen to match the expected exposure/gray level values under nominal operating condition with air between the detector and the x-ray source.

Figure 8:
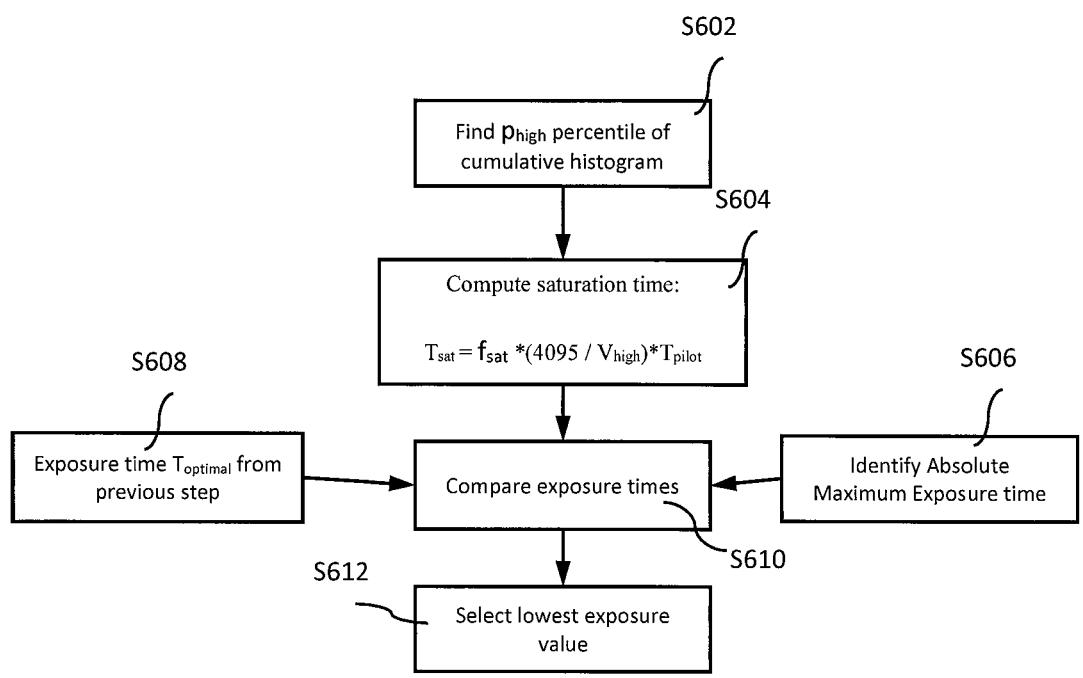
FIG. 8 is a diagram that shows how to ensure that a resulting image is not saturated.

Turning now to FIG. 8, the estimated exposure time $T_{est}$ can be determined by determining the time it takes for pixels of the detector 2 to become saturated and comparing that time with $T_{optimal}$ and a maximum possible exposure time $T_{max}$. The minimum of the three can be chosen such that a minimum dose will be delivered to the detector 2. The $p_{high}$ percentile of the cumulative histogram can be determined in Step S602. A saturation time for the detector pixels is then determined in Step S604. Having an estimated optimal remaining exposure time S608 and an absolute maximum exposure time, the lowest exposure time can be determined to be used in taking the additional projection image(s) that may be combined with the pilot projection image. These steps are explained further below.

1. An estimated saturation exposure time ($T_{sat}$) is determined using the maximum image gray level value which is typically 4095.

$$T_{sat} = f_{sat} * (4095/V_{high}) * T_{pilot}$$

wherein $V_{high}$ is the $p_{high}$ percentile of the pilot projection image, $T_{pilot}$ is the exposure time of the pilot projection image and $f_{sat}$ is the maximum fraction of the detector range that the summed image is expected to occupy. In an embodiment herein, $f_{sat}$ is less than 1 and thus $T_{sat}$ has a value less than the time it takes to reach saturation.

2. The estimated remaining exposure time ($T_{est}$) is then determined as follows.

$$T_{est} = \min(T_{optimal}, T_{sat}, T_{max})$$

wherein $T_{optimal}$ is the estimated optimal remaining exposure time, $T_{sat}$ is the estimated saturation exposure time and $T_{max}$ is the maximum possible exposure time for any scan taking into consideration, for example, a maximum patient head size and a maximum distance of the patient from the x-ray source. In an embodiment herein, $T_{max}$ is 280 msec.

In another embodiment herein, if $T_{sat}$ is less than $T_{optimal}$, the remaining exposure may be split into multiple images and all of the images may then be summed.

3. The estimated remaining exposure time is then compared with a minimum settable exposure time ($T_{minset}$) for the system 1, 1a. The minimum of the two determines the final estimated remaining exposure time.

$$T_{est} = \max(T_{est}, T_{minset})$$

Figure 9:
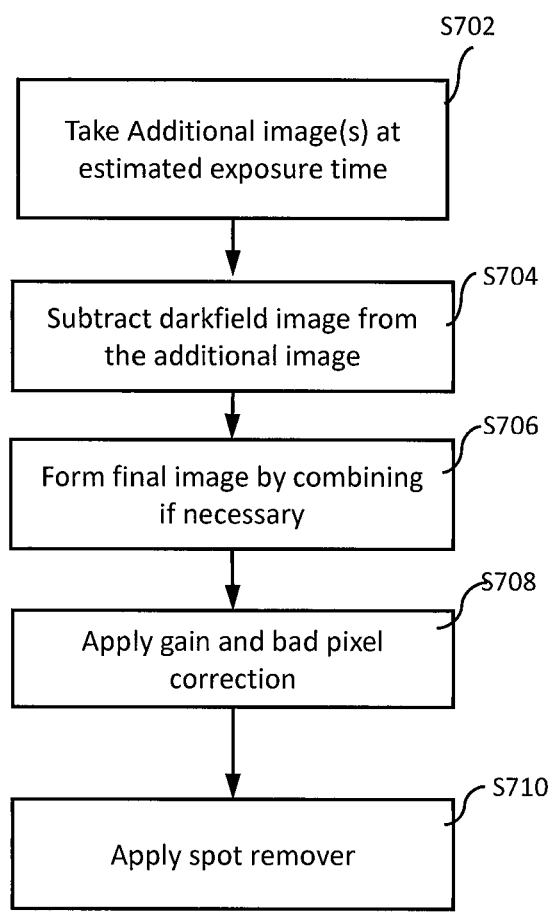
FIG. 9 is a diagram illustrating how an additional projection image is taken and used to create a final image.

Turning now to FIG. 9, the final image may be obtained beginning at Step S702 by taking an additional projection image using the estimated remaining exposure time. In a tomosynthesis system 1a, multiple additional projections may be taken at different angles relative to the z axis wherein the additional projection images may be final images, thus eliminating the need to combine the pilot projection image with the additional projection images. In Step S704, the dark field image is subtracted from the additional projection image(s) to remove any contributions to the additional projection image(s) by dark current. The resulting image can be combined with the pilot projection image to form a final image in Step S706 in an x-ray system 1.

Standard gain and bad pixel correction methods can then be applied to the final image to remove noise thereof in Step S708 and spot removing procedures can also be applied to the final image in Step S710 to remove X-ray speckles from the final image.

By virtue of using the computer system 6 to perform at least part of the process shown in FIGS. 4-9 and described above, the x-ray system 1 can be controlled to acquire a scout shot or pilot projection image at a low dose prior to taking an additional projection image at the correct dose to generate a final image with a combined dose that is appropriate for the specific dental anatomy being imaged, thus, thus potentially lowering the x-ray exposure to the patient and reducing image acquisition time, even while generating and presenting clinical information of high value and utility. Similarly, the tomosynthesis x-ray system 1a can be controlled to acquire a pilot projection image at a low dose prior to taking an additional projection image for each projection in a tomosynthesis scan at the correct dose such that each additional projection image is a final image. In this case, since the angle at which the scout shot is taken, e.g. 0° differs from the angles at which the most of the additional projection images are taken, the image of the scout shot/pilot projection image may not be combined with the additional projection images. Instead an appropriate remaining exposure time for each additional projection image may be determined from the single scout shot/pilot projection such that each additional projection image is a final image for the corresponding tomosynthesis projection.

In view of the foregoing description, it can be appreciated that the example embodiments described herein provide systems, methods, apparatuses, and computer programs products for automatically determining exposure time for an intraoral image. In turn, the reduced dosages and automatic determination of exposure times for all patients may simplify a clinician user's diagnosis and treatment planning tasks, since manual methods of selecting intraoral x-ray exposure settings from a predetermined list based on the expected patient characteristics, nominal source characteristics, the expected x-ray filtration, the expected source-detector separation, and the expected x-ray sensor characteristics, etc., may be eliminated.

As will be appreciated by those of skill in the relevant art(s) in view of this description, the example aspects described herein can be implemented using a single computer or using a computer system that includes multiple computers each programmed with control logic to perform various of the above-described functions.

The various embodiments described above have been presented by way of example and not limitation. It will be apparent to persons skilled in the relevant art(s) that various changes in form and detail can be made therein (e.g., different hardware, communications protocols, and the like) without departing from the spirit and scope of the present disclosure. Thus, the present disclosure should not be limited by any of the above-described exemplary embodiments, but should be defined only in accordance with the following claims and their equivalents.

In addition, it should be understood that the attached drawings, which highlight functionality described herein, are presented as illustrative examples. The architecture of the present disclosure is sufficiently flexible and configurable, such that it can be utilized and navigated in ways other than that shown in the drawings.

Moreover, the example embodiments described herein are not limited to intraoral x-ray and intraoral tomosynthesis x-ray imaging. The example embodiments described herein can be used to perform scans of other anatomical regions.

Further, the purpose of the Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present disclosure in any way. It is also to be understood that the processes recited in the claims need not be performed in the order presented.

What is claimed is:

1. A method for automatically determining a required exposure time for an intraoral x-ray projection image, the method comprising:
    acquiring a low dose pilot projection image of an object to be imaged;
    performing a sanity check to ensure that a usable exposure is attainable;
    estimating a remaining required exposure time for obtaining one or more additional projection images, the estimating including determining that one or more final images will not be saturated by computing an estimated saturation exposure time required for saturation of an x-ray detector, and comparing said estimated saturation exposure time required for saturation with at least one of an estimated optimal exposure time and a maximum possible exposure time and
    responsive to determining that the one or more final images will not be saturated, obtaining the one or more additional projection images for one or more final images using the estimated remaining required exposure time such that a dose delivered to the x-ray detector is influenced by patient specific dental anatomy.

2. The method according to claim 1, wherein the obtaining includes performing x-ray imaging and wherein the pilot projection image and one additional projection image are combined to form one final image.

3. The method according to claim 1, wherein the obtaining includes performing tomosynthesis x-ray imaging, wherein the one or more additional projection images are final images and wherein the final images are reconstructed into tomographic images, and wherein the tomographic images are tomosynthesis images.

4. The method according to claim 1, wherein the acquiring includes performing a setup comprising selecting an expectation of an image quality wherein the image quality is discrete or according to a sliding scale.

5. The method according to claim 1, further comprising processing the pilot projection image and the one or more additional projection images by performing a dark field image subtraction.

6. The method according to claim 1, wherein the performing includes calculating a cumulative histogram of said pilot projection image and removing contributions by at least one of (i)defective pixels, (ii)metal regions of the object to be imaged and (iii)tissue regions of the object to be imaged to said cumulative histogram and,
    wherein the removing further includes at least one of (i)determining a pilot projection image range and (ii) calculating a high threshold and a low threshold using the determined pilot projection image range.

7. The method according to claim 6, wherein the estimating further includes determining a median gray level value of pixels between the determined high and low thresholds,
    wherein the median gray level value represents teeth and trabeculae.

8. The method according to claim 7, wherein the estimating further includes determining an estimated optimal exposure time using a target value, the determined median gray level value and a pilot projection image exposure time.

9. The method according to claim 1, further comprising processing the one or more final images by applying gain and bad pixel correction.

10. The method according to claim 1, further comprising displaying at least one of the one or more final images and an exposure quality on a display unit.

11. A system for automatically determining a required exposure time for an intraoral x-ray image, the system comprising:
    at least one processor operable to:
        acquire a low dose pilot projection image of an object to be imaged;
        perform a sanity check to ensure that a usable exposure is attainable;
        estimate a remaining required exposure time for obtaining one or more additional projection images by determining that one or more final images will not be saturated by computing an estimated saturation exposure time required for saturation of an x-ray detector, and comparing said estimated saturation exposure time required for saturation with at least one of an estimated optimal exposure time and a maximum possible exposure time and
        responsive to determining that the one or more final images will not be saturated, obtain the one or more additional projection images for one or more final images using the estimated remaining required exposure time such that a dose delivered to the x-ray detector is influenced by patient specific dental anatomy.

12. The system according to claim 11, wherein the processor is operable to perform x-ray imaging and wherein the pilot projection image and one additional projection image are combined to form one final image.

13. The system according to claim 11, wherein the processor is operable to perform tomosynthesis imaging wherein the one or more additional projection images are final images and wherein the final images are reconstructed into tomographic images, and wherein the tomographic images are tomosynthesis images.

14. The system according to claim 11, wherein the processor is operable to perform a setup comprising selecting an expectation of an image quality wherein the image quality is discrete or according to a sliding scale.

15. The system according to claim 11, wherein the processor is operable to further process the pilot projection image and the one or more additional projection images by performing a dark field image subtraction.

16. The system according to claim 11, wherein the processor is operable to calculate a cumulative histogram of said pilot projection image and to remove contributions by at least one of (i)defective pixels, (ii)metal regions of the object to be imaged and (iii)tissue regions of the object to be imaged to said cumulative histogram and, wherein the removing by the processor further includes at least one of (i)determining a pilot projection image range and (ii)calculating a high threshold and a low threshold using the determined pilot projection image range.

17. The system according to claim 16, wherein the processor is further operable to determine a median gray level value of pixels between the determined high and low thresholds, wherein the median gray level value represents teeth and trabeculae.

18. The system according to claim 17, wherein the processor is further operable to determine an estimated optimal exposure time using a target value, the determined median gray level value and a pilot projection image exposure time.

19. The system according to claim 11, wherein the processor is operable to provide at least one of the one or more final images and an exposure quality to a display unit.

20. A non-transitory computer-readable storage medium storing a program which, when executed by a computer system, causes the computer system to perform a procedure comprising:

acquiring a low dose pilot projection image of an object to be imaged;

performing a sanity check to ensure that a usable exposure is attainable;

estimating a remaining required exposure time for obtaining one or more additional projection images, the estimating including determining that one or more final images will not be saturated by computing an estimated saturation exposure time required for saturation of an x-ray detector, and comparing said estimated saturation exposure time required for saturation with at least one of an estimated optimal exposure time and a maximum possible exposure time and responsive to determining that the one or more final images will not be saturated, obtaining the one or more additional projection images for one or more final images using the estimated remaining required exposure time such that a dose delivered to the x-ray detector is influenced by patient specific dental anatomy.

\* \* \* \* \*